United States Patent
Satterly et al.

(10) Patent No.: US 10,379,122 B1
(45) Date of Patent: Aug. 13, 2019

(54) METHODS FOR NORMALIZING BACKGROUND EFFECTS IN MULTIPLEX IMMUNOASSAYS

(71) Applicant: The United States of America as represented by the Secretary of the Army on behalf of the U.S. Army Medical Research and Material Command, Washington, DC (US)

(72) Inventors: Neal G. Satterly, Lawrenceville, GA (US); Randal J. Schoepp, Frederick, MD (US)

(73) Assignee: The United States of America as represented by the Secretary of the Army on behalf of the U.S. Army Medical Research and Materiel Command

( * ) Notice: Subject to any disclaimer, the term of this patent is extended or adjusted under 35 U.S.C. 154(b) by 221 days.

(21) Appl. No.: 15/232,540

(22) Filed: Aug. 9, 2016

Related U.S. Application Data

(60) Provisional application No. 62/203,165, filed on Aug. 10, 2015.

(51) Int. Cl.
*G01N 31/00* (2006.01)
*G01N 33/53* (2006.01)
*G01N 33/569* (2006.01)
*G01N 33/58* (2006.01)
*G01N 33/553* (2006.01)

(52) U.S. Cl.
CPC ..... *G01N 33/56983* (2013.01); *G01N 33/553* (2013.01); *G01N 33/582* (2013.01)

(58) Field of Classification Search
None
See application file for complete search history.

(56) References Cited

PUBLICATIONS

Anderson et al. (BioTechniques, vol. 43, pp. 806-811, Dec. 2007).*
Yang etal. (Cytometry, Part A, vol. 71A, pp. 625-631,2007).*

* cited by examiner

*Primary Examiner* — Lisa V Cook
(74) *Attorney, Agent, or Firm* — Elizabeth Arwine, Esq.

(57) ABSTRACT

Disclosed herein methods, compositions, and kits for obtaining a normalized measured amount of a target in a sample by measuring the amount of the target in the sample by contacting the sample with a detection reagent, measuring the amount of a ligand known to be absent in the sample being tested by contacting the sample with a control reagent, and obtaining the normalized measured amount of the target by calculating the ratio of the measured amount of the target to the measured amount of the ligand.

16 Claims, 12 Drawing Sheets

METHODS FOR NORMALIZING BACKGROUND EFFECTS IN MULTIPLEX IMMUNOASSAYS

ACKNOWLEDGEMENT OF GOVERNMENT SUPPORT

This invention was made by employees of the United States Army Medical Research and Materiel Command, which is an agency of the United States Government. The Government has certain rights in the invention.

BACKGROUND OF THE INVENTION

1. Field of the Invention

The present invention relates to methods for normalizing matrix background effects in multiplex immunoassays.

2. Description of the Related Art

Immunological-based assays, such as ELISA or MAGPIX assays are plagued with background issues. Almost all clinical and environmental samples will generate a background signal. This background signal can vary tremendously from sample to sample. Thus, it becomes exceedingly difficult to identify a sample positive for target antigen and with low background in the mist of other samples negative for the antigen and with very high background. Therefore, immunological-based assays display higher consistency when detecting samples with very high amounts of antigen, and display poor consistency when detecting samples with small amounts of antigen.

Thus, a need exists for methods and control reagents that provide consistent immunoassay results between samples that are positive for a given target antigen and have a relatively low background and samples that are negative for the given target antigen and have a relatively high background.

SUMMARY OF THE INVENTION

In some embodiments, the present invention provides methods for obtaining a normalized measured amount of a target in a sample using a multiplex immunoassay which comprises measuring the amount of the target in the sample by contacting the sample with a detection reagent, measuring the amount of a ligand known to be absent in the sample being tested by contacting the sample with a control reagent, and obtaining the normalized measured amount of the target by calculating the ratio of the measured amount of the target to the measured amount of the ligand. In some embodiments, the present invention provides methods for characterizing a sample as containing or not containing a target which comprises using a multiplex immunoassay to measure the amount of the target in the sample by contacting the sample with a detection reagent and the amount of a ligand known to be absent in the sample by contacting the sample with a control reagent, obtaining the normalized measured amount of the target by calculating the ratio of the measured amount of the target to the measured amount of the ligand, and characterizing the sample as containing the target where the normalized measured amount is above the mean or outlier threshold of negative control samples. In some embodiments, the ratio of the measured amount of the target to the measured amount of the ligand is the ratio of the observed amount of bound detection reagent to the observed amount of bound control reagent. For example, where fluorescent labels are used, the ratio is the mean fluorescent intensity (MFI) of the bound detection reagent to the MFI of the control reagent.

In some embodiments, the sample is a blood, plasma, serum sample, or another complex matrix that can generate a non-specific signal. In some embodiments, the amount of the target is measured by measuring the amount of the detection reagent complexed with the target. In some embodiments, the amount of the ligand is measured by measuring the amount of the control reagent complexed with the ligand. According to the present invention, the detection reagent and the control reagent do not react or bind to each other, the detection reagent does not cross react with the ligand, and the control reagent does not cross react with the target. In some embodiments, the detection reagent specifically binds the target. In some embodiments, the control reagent specifically binds the ligand. In some embodiments, the target is an antigen and the detection reagent is an antibody or fragment thereof that specifically binds or was raised against the target. In some embodiments, the target is an antibody against an antigen and the detection reagent is the antigen or an antibody that binds the antibody against the antigen. In some embodiments, the control reagent is an antibody or fragment thereof that specifically binds or was raised against the ligand. In some embodiments, the ligand is an antibody or fragment thereof that specifically binds or was raised against the ligand. In some embodiments, the control reagent has a detectable label, such as a fluorescent tag or an electrochemoluminescent tag, bound thereto.

In some embodiments, either the ligand or the control reagent is a bacteriophage protein. In some embodiments, the bacteriophage protein is an M13 bacteriophage protein. As used herein, an "M13 bacteriophage protein" includes proteins obtained or derived from an M13 bacteriophage such as those provided in Henry & Pratt (1969) PNAS USA 62(3): 800-807, Sidhu et al. (2007) Methods Mol Biol. 352:205-219, and WO2009086116, which are herein incorporated by reference in their entirety.

In some embodiments, the control reagent is immobilized on the surface of an immunoassay bead. In some embodiments, the immunoassay bead comprises a detectable label such as a fluorescent tag or an electrochemoluminescent tag. In some embodiments, the immunoassay bead is paramagnetic or magnetic. In some embodiments, the immunoassay bead is suitable for use in a multiplex immunoassay. In some embodiments, the multiplex immunoassay is based on xMAP® (Multi-Analyte Profiling) technology by Luminex Corporation (Austin, Tex.). In some embodiments, the multiplex immunoassay is based on the MAGPIX® platform by Luminex.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1, FIG. 2, FIG. 3, and FIG. 4 are graphs showing the ELISA (FIG. 1) and MAGPIX® (FIG. 2) lower limit of detection (LLOD) determination for *Lassa virus* (LASV) IgM-detection using native antigens and ELISA (FIG. 3) and MAGPIX® (FIG. 4) LLOD determination for *Ebola virus* (EBOV) IgM-detection using native antigens. The negative control (N.C.) was normal nonhuman primate (NHP) serum. The cutoff for positive detection is defined as 2.5× the average N.C. absorbance (ELISA) or MFI (MAGPIX®) value. Yellow bars (FIG. 1=3 right bars, FIG. 2=6 right bars, FIG. 3=4 right bars, FIG. 4=8 right bars) a positive detection; black bars indicate no significant difference from the N.C. Error bars for each datum point represent the standard deviation of n≥3.

FIG. 5, FIG. 6, FIG. 7, and FIG. 8 are graphs showing ELISA (FIG. 5) and MAGPIX® (FIG. 6) LLOD determination for LASV IgM-detection using recombinant antigens and ELISA (FIG. 7) and MAGPIX® (FIG. 8) LLOD determination for EBOV IgM-detection using recombinant antigens. The negative control (N.C.) was normal NHP serum. The cutoff for positive detection is defined as 2.5× the average N.C. absorbance (ELISA) or MFI (MAGPIX®) value. Yellow bars (FIG. 5=5 right bars, FIG. 6=6 right bars, FIG. 7=5 right bars, FIG. 8=8 right bars) indicate a positive detection; black bars indicate no significant difference from the N.C. Error bars for each datum point represent the standard deviation of n≥3.

FIG. 9 and FIG. 10 are graphs showing the consistency of the MAGPIX® LASV (FIG. 9) and MAGPIX® EBOV (FIG. 10) IgM-detection assays at the LLOD. Blue (square) data points represent 30 replicates of the respective IgM-positive serum sample diluted to the previously observed LLOD. The solid line represents the mean MFI value for 30 unique, normal serum samples (N.C.). Error bars on each end of the solid line show the standard deviation for the 30 N.C. samples. The broken line represents the mean MFI value for N.C. samples multiplied by 2.5 (LLOD cutoff).

FIG. 11, FIG. 12, FIG. 13, and FIG. 14 are graphs showing ELISA (FIG. 11) and MAGPIX® (FIG. 12) LLOD determination for LASV-GPC antigen-detection using purified LASV (Josiah) diluted in buffer and ELISA (FIG. 13) and MAGPIX® (FIG. 14) LLOD determination for LASV-NP antigen-detection using LASV tissue culture supernatant diluted in buffer. The negative control (N.C.) for LASV-GPC was purified pichinde virus, a new-world arenavirus, used at a pfu/mL equal to the 1:100 dilution of purified LASV. The N.C. for LASV-NP was EBOV tissue culture supernatant. The cutoff for positive detection is defined as 2.5× the average N.C. absorbance (ELISA) or MFI (MAGPIX®) value. Yellow bars (FIG. 11=2 right bars, FIG. 12=4 right bars, FIG. 13=2 right bars, FIG. 14=6 right bars) indicate a positive detection; black bars indicate no significant difference from the N.C. Error bars for each datum point represent the standard deviation of n≥3.

FIG. 15, FIG. 16, FIG. 17, FIG. 18 are graphs showing ELISA (FIG. 15) and MAGPIX® (FIG. 16) LLOD determination for EBOV-GP antigen-detection using EBOV tissue culture supernatant diluted in buffer and ELISA (FIG. 17) and MAGPIX® (FIG. 18) LLOD determination for EBOV-VP40 antigen-detection using EBOV tissue culture supernatant diluted in buffer. The negative control (N.C.) was LASV tissue culture supernatant. The cutoff for positive detection is defined as 2.5× the average N.C. absorbance (ELISA) or MFI (MAGPIX®) value. Yellow bars (FIG. 15=5 right bars, FIG. 16=6 right bars, FIG. 17=6 right bars, FIG. 18=10 right bars) indicate a positive detection; black bars indicate no significant difference from the N.C. Error bars for each datum point represent the standard deviation of n≥3.

FIG. 19 is a graph showing the consistency of the MAGPIX® LASV-NP antigen-detection assay. Each datum point represents a Z-score value of the LASV-NP/M13 MFI ratio. Blue data points (without an arrow pointing thereto) represent normal serum samples; the blue datum point outlined in black (near 2.3e5 pfu/mL (1:100)) represents the highest unspiked ratio Z-score. Red data points (with arrows except for the 9.2e5 pfu/mL arrow) represent ratio Z-scores from serum samples spiked with serial dilutions of LASV tissue culture supernatant. Yellow data points (cluster at the 9.2e5 pfu/mL arrow) represent ratio Z-scores from 15 serum samples spiked with $9.2\times10^5$ pfu/mL (1:25).

FIG. 20 is a graph showing the consistency of the MAGPIX® EBOV-VP40 antigen-detection assay. Each data point represents an EBOV-VP40/M13 MFI ratio Z-score. Blue data points (forming a line) represent normal serum samples; the blue datum point outlined in black represents the highest unspiked ratio Z-score. Red data points (with arrows pointed thereto except for the 3.4e4 pfu/mL (1:500) arrow) represent ratio Z-scores from serum samples spiked with serial dilutions of EBOV tissue culture supernatant. Yellow data points (cluster at the 3.4e4 pfu/mL (1:500) arrow) represent ratio Z-scores from 15 serum samples spiked with $3.4\times10^4$ pfu/ml.

FIG. 21 is a graph showing the mean fluorescent intensities (MFI) for EBOV that was determined without normalization for each sample in triplicate. The circles are unspiked samples, the squares with the X are the spiked samples, and the horizontal lines from bottom to top are: the mean MFI of all samples, one standard deviation above the mean MFI, two standard deviations above the mean MFI, respectively.

FIG. 22 is a graph showing the calculated and plotted ratio of the MFI of EBOV/M13 (normalized MFI) for each sample. The circles are unspiked samples, the squares with the X are the spiked samples, and the horizontal lines from bottom to top are: the mean MFI of all samples, one standard deviation above the mean MFI, two standard deviations above the mean MFI, respectively.

FIG. 23 is a graph showing the outlier threshold of the samples without normalization that were determined using interquartile statistical methods. The horizontal line indicates the outlier threshold that is the interquartile range multiplied by 4 added to the MFI value demarcating the start of the 4th quartile (4×IQR+MFI value starting the 4th quartile).

FIG. 24 is a graph showing the outlier threshold of the samples with normalization that were determined using interquartile statistical methods. The horizontal line indicates the outlier threshold that is the interquartile range multiplied by 4 added to the ratio of the MFI EBOV/M13 value demarcating the start of the 4th quartile (4×IQR+MFI EBOV/M13 ratio starting the 4th quartile).

DETAILED DESCRIPTION OF THE INVENTION

As disclosed herein, the present invention relates to methods and reagents for normalizing the results of immunoassays. Normalization according to the present invention is capable providing immunoassay results that have a sensitivity (i.e., true positive rate) of about 99% or more and a specificity (i.e., true negative rate) of about 100%. Thus, the present invention provides a technological improvement over existing immunoassay methods.

Comparison Between Conventional ELISA, Multiplex Assay, and Multiplex Assay with Normalization

Figure 11:
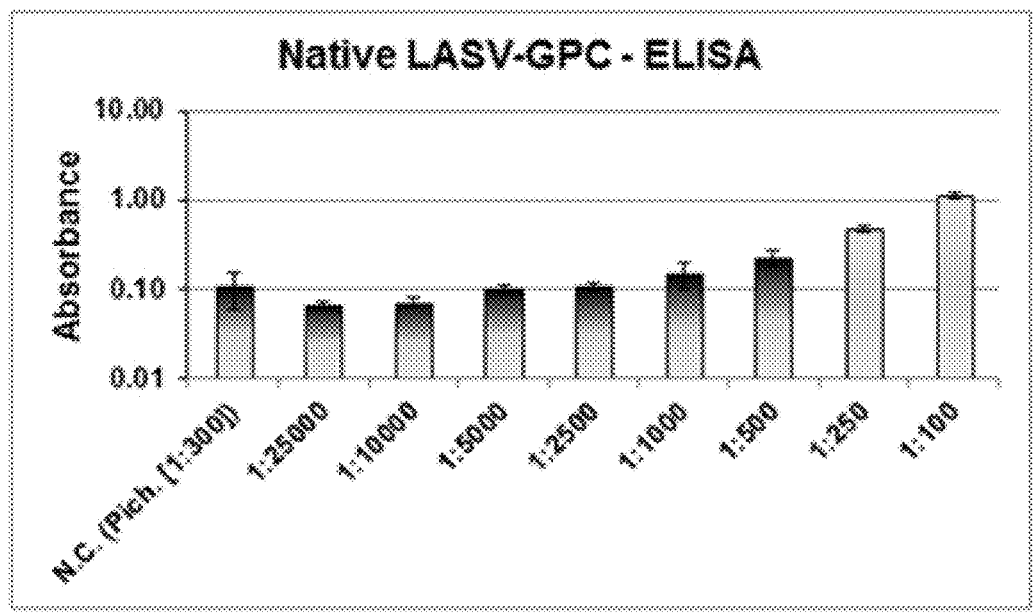

Hemorrhagic fevers are part of the normal disease burden in Africa. In the developed world, they are a concern because of their potential use as bioterrorism agents. *Lassa virus* (family: Arenaviridae) and *ebolaviruses* (family: Filoviridae) are hemorrhagic fever viruses that are endemic in several African countries. Disease outbreaks with these viruses have significant medical and social impacts. Case fatality rates can be up to 20% for *Lassa* (LASV) and up to 90% for *ebolaviruses*. Their high mortality rates combined with their ease of transmission and lack of vaccines or effective treatments render them extremely dangerous pathogens.

As disclosed herein, the performances of conventional enzyme-linked immunosorbent assays (ELISA) (Bowen et al. (2000) J. Virol. 74:6992-7004; and Ksiazek et al. (1999) J. Infect. Dis. 179 Suppl 1:S192-S198) are compared with that of a multiplex assay platform, MAGPIX® using the Luminex xMAP® technology, for the detection of LASV and *Ebola virus* (EBOV) antigens and IgM antibodies against LASV and EBOV. Both native and recombinant viral proteins as targets in IgM immunoassays and the consistency of the MAGPIX® platform in complex matrices were evaluated. This work demonstrates that the MAGPIX® platform is a new and powerful diagnostic tool for scientists and clinicians for the detection and identification of LASV, EBOV, and other diseases that rely on ELISA as a component of an orthogonal system.

As disclosed herein, the lower limit of detection (LLOD) of ELISA and MAGPIX® for the detection of LASV and EBOV IgM antibodies was compared using both native and recombinant antigens. Without exception, the MAGPIX® platform was more sensitive. The MAGPIX® assays were capable of detecting 10 times less concentrated IgM than ELISA. Similar results were observed with LASV and EBOV antigen-detection. The MAGPIX® assays were capable of detecting 20-25 times less viral antigen than ELISA. This increased capacity to detect lower levels of antibody and antigen by the MAGPIX® instrument can result in earlier diagnosis of infection and earlier treatment that would reduce the morbidity or mortality associated with these diseases.

Consistency of assay performance is integral to confidence in the results. To demonstrate the consistency of the MAGPIX®'s ability to detect the presence of IgM antibodies, the assay was repeated 30 times using the IgM-detection LLOD of LASV (1:25,000) and EBOV (1:25,000) and the results were compared to 30 unique, negative human serum samples. Among these samples, no false negatives from the positive samples diluted to the LLOD were observed. The percent coefficient of variance (% CV) for these IgM-detection assays never rose above 10%, demonstrating the excellent consistency produced from the MAGPIX® platform.

Measuring MAGPIX® consistency for antigen-detection assays required a more elegant assay. Since the influence of matrix effects from one serum to another can vary widely, fluctuations in LLOD due to these effects are a common problem with antigen-detection immunoassays. To remedy this issue, an internal control that effectively normalized the data obtained in antigen detection assays for LASV and EBOV was designed. This solution, which arises from the multiplexing capability of the MAGPIX® platform, allows one to make accurate determinations regarding an assay's consistency from one serum sample to the next. This has been found to be a much more facile and inexpensive solution (since M13 mAbs are relatively inexpensive) than incorporating exotic blocking agents into the buffers. Once the background was normalized, the MFI of 15 unique serum samples spiked with the LLOD concentration of LASV or EBOV were measured. From these samples, a % CV of 12% and 10%, respectively, was observed, thereby demonstrating the excellent consistency of these assays when performed on the MAGPIX® platform.

The data presented here show that the MAGPIX® platform is a powerful tool in early diagnosis of LASV and EBOV. The data also show that this platform outperforms ELISA when used to detect the presence of LASV and EBOV.

Materials and Methods

Antibodies

Capture monoclonal antibody (mAb) common identification codes are as follows: L52-85-6-BG12 for LASV-GPC; L52-2159-15 for LASV-NP; Z-DA06-AH05 for EBOV-GP; and M-HD06-A10A for EBOV-VP40. Covalent linking of capture mAbs to microspheres was achieved using the Luminex microspheres coupling kit (Luminex, Austin, Tex.) according to the instructions. Biotinylated detection mAb common identification codes are as follows: L52-2074-7A for LASV-GPC; L52-189-13 for LASV-NP; DA01-A5-B11 for EBOV-GP; and BMD04-BD07-AE11 for EBOV-VP40. Biotinylation of detection mAbs was achieved using the EZ-Link® Sulfo-NHS-LC-Biotinylation Kit (Thermo Fisher Scientific, Waltham, Mass.) according to the instructions.

Serum samples from nonhuman primates (NHP), Rhesus macaque (*Macaca mulatta*), infected with LASV and EBOV were used to evaluate the diagnostic assays. The LASV and EBOV infected samples were obtained from banked serum samples from earlier studies.

Viruses

Confluent Vero cells were infected with LASV, Josiah strain in Dulbecco's Modified Eagle's Medium (DMEM), 10% FBS, 1% L-glutamine, and 0.1% gentamicin. Cells were harvested on day 5. The supernatant was cleared of cellular debris by low-speed centrifugation, titers were determined by plaque assay, and the virus was inactivated via gamma-radiation. Purified LASV was produced by conventional sucrose gradient.

Confluent Vero Cells were infected with EBOV+, Zaire strain in Eagle's Minimum Essential Medium (EMEM) supplemented with 5% FBS, 1% L-glutamine, and 0.5% penicillin/streptomycin. Cells were harvested on day 7. The supernatant was cleared of cellular debris by low-speed centrifugation, titers were determined by plaque assay, and the virus was inactivated via gamma-radiation.

Confluent Vero cells were infected with Pichende virus, CoAN3739 strain in Eagle's Minimum Essential Medium (EMEM) supplemented with 5% FBS, 1% HEPES, 1% penicillin/streptomycin, 0.1% amphotericin, and 0.1% gentamicin. Cells were harvested on day 5. The supernatant was cleared of cellular debris by low-speed centrifugation, titers were determined by plaque assay, and the virus was inactivated via gamma-radiation.

Recombinant Viral Proteins

Expression constructs for recombinant viral proteins were produced by amplification of specific gene regions by RT-PCR from LASV or EBOV genomic material. For LASV proteins, NP and GPC, RNA was extracted from LASV, Josiah strain; for EBOV, GP, and VP40, RNA was extracted from EBOV, Zaire 95 strain. LASV-GPC and EBOV-GP genes were separately cloned into pCDNA3.1(+) myc/his (Life Technologies, Grand Island, N.Y.). LASV-NP and EBOV-VP40 genes were separately cloned into pCDNA3.1 (+) myc/his (Life Technologies) modified to contain maltose-binding protein gene directly up-stream of the viral gene insert. Vectors were transiently transfected into 293T cells with Lipofectamine 2000 (Life Technologies) according to the instructions. The cells were harvested 48 hours post-transfection. For recLASV-NP and recEBOV-VP40, cells were lysed with Lysis Buffer (LB) (20 mM HEPES, 110 mM potassium acetate, 2 mM magnesium chloride (pH 7.5)) supplemented with 1% Tween20 (Sigma-Aldrich, St. Louis, Mo.) and complete, EDTA-free protease-inhibitor cocktail (Roche Diagnostics, Indianapolis, Ind.). For recLASV-GPC and recEBOV-GP, cells were lysed with Nickel Buffer (NB) (20 mM sodium phosphate, 500 mM sodium chloride, 20 mM imidazole) supplemented with 1% Tween20 (Sigma) and complete, EDTA-free protease-inhibitor cocktail (Roche Diagnostics). Lysates were centrifuged at 14,000 g for ten minutes and the pellet was discarded. The expressed recLASV-NP and recEBOV-VP40 were purified by batch with amylose resin (New England Biolabs, Ipswich, Mass.). The expressed recLASV-GPC and recEBOV-GP was purified by batch with Ni-NTA agarose (Qiagen, Valencia, Calif.). After binding, the resins were washed with LB for a total of five washes. The bound recLASV-NP and recEBOV-VP40 protein was eluted with LB supplemented with 20 mM maltose (Sigma-Aldrich) and the bound recLASV-GPC and recEBOV-GP was eluted with NB supplemented with 200 mM imidazole. Eluates were concentrated with an Amicon® Ultra (10K) Centrifugal Filter (EMD Millipore, Billerica, Mass.). After concentrating the eluted protein, buffer exchange with 1× phosphate-buffered saline (PBS, pH=7.4) was performed in the same centrifugal filter.

ELISA IgM Detection Assays

For these assays, a multi-level sandwich was created. In summary, the sandwich consisted of (in order): plate/anti-IgM mAb/test serum/antigen cocktail (native or recombinant)/antigen-specific mAb cocktail/and biotinylated detector mAb.

Figures 1, 2:
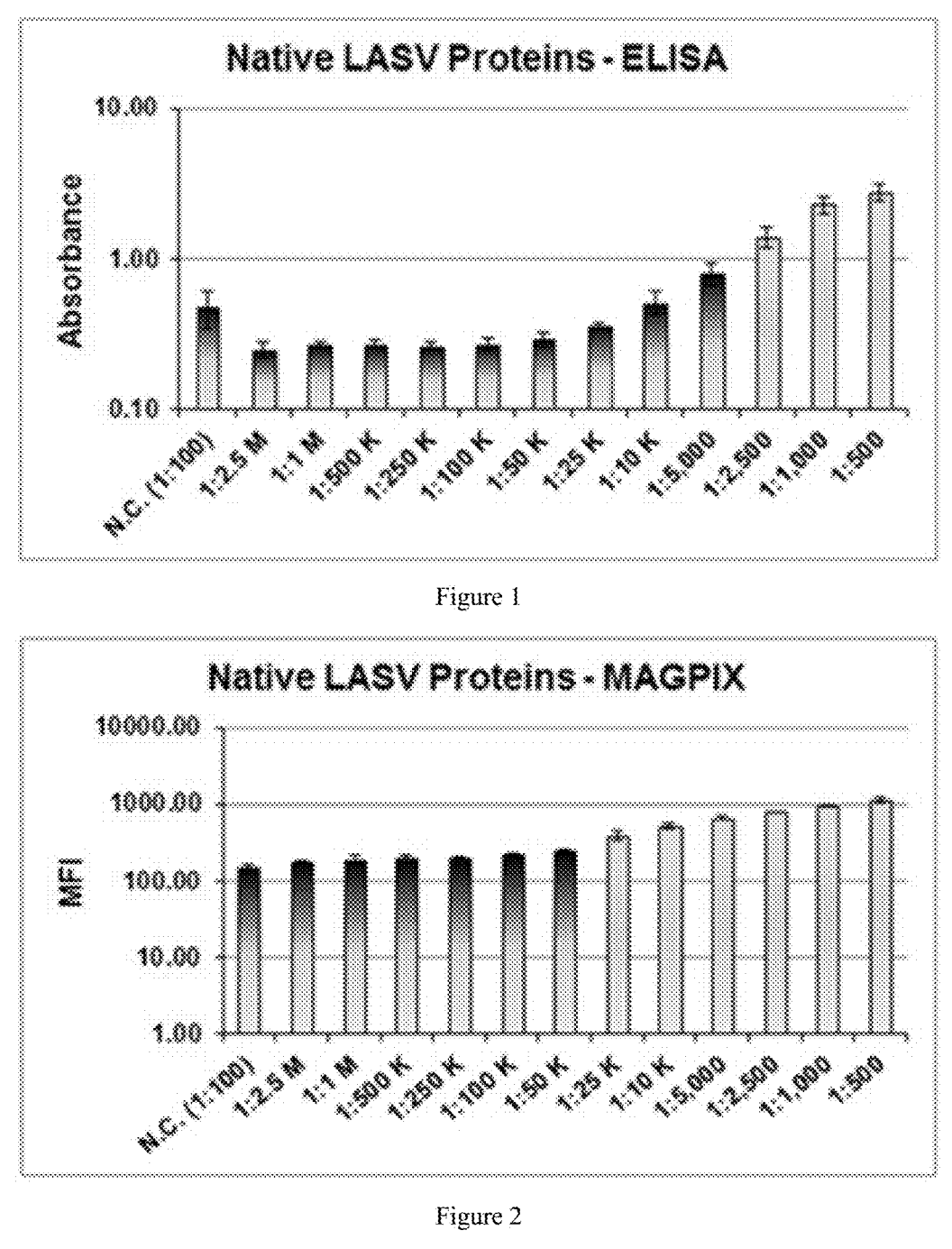

Costar Serocluster™ vinyl, 96-well ELISA plates (Corning, Tewksbury, Mass.) were coated overnight at 4° C. with a mAb specific for the μ-chain of human IgM (Kirkegaard & Perry Laboratories (KPL), Gaithersburg, Md.). The anti-μ antibody was used at 4 μg/mL in PBS. After coating, serial dilutions of a confirmed-positive IgM serum sample from LASV- or EBOV-infected NHP were made in PBS with 5% skim milk (PBS-S) and added to the plates. The plates were incubated at 37° for 1 hour, and then washed three times with PBS containing 0.1% Tween20 (PBS-T). For FIG. 1 to FIG. 4, LASV or EBOV antigens from tissue culture supernatant were diluted with PBS-S to working concentrations of $5.7 \times 10^5$ or $3.4 \times 10^6$, respectively, and added to the plates. For FIG. 5 to FIG. 8, a cocktail of recombinant LASV antigens (GPC and NP) or a cocktail of recombinant EBOV antigens (GP and VP40) was added to the plates. Each recombinant cocktail constituent was used at 10 ng/μL μL in PBS-S. All plates were incubated at 37° C. for 1 hour, and then washed three times with PBS-T. Plates testing for the presence of LASV-specific IgM next received a cocktail of two biotinylated detector mAbs diluted to 4 μg/mL with PBS-S. One mAb was specific for glycoprotein complex (GPC (L52-2074-7A)) and the other for nucleocapsid protein (NP (L52-189-13)). Plates testing for the presence of EBOV-specific IgM also received a cocktail of two biotinylated detector mAbs diluted to 4 μg/mL with PBS-S. One mAb was specific for glycoprotein GP1 (DA01-A5-B11) and the other for VP40 (BMD04-BD07-AE11). After the respective cocktails were added, all plates were incubated at 37° C. for 1 hour, and then washed three times with PBS-T. Next, all plates received HRP-linked streptavidin (Thermo Fisher Scientific) diluted to 25 μg/mL with PBS-S, were incubated at 37° C. for 1 hour, and then washed three times with PBS-T. Lastly, all plates received ABTS® peroxidase substrate solution (KPL) and were incubated at 37° C. for 1 hour. The optical densities (OD) were determined at 410 nm in an automated ELISA plate reader.

MAGPIX® IgM Detection Assays

For these assays, a multi-level sandwich was created. In summary, the sandwich consisted of (in order): microspheres/anti-IgM mAb/test serum/antigen cocktail (native or recombinant)/antigen-specific mAb cocktail/and biotinylated detector mAb.

MagPlex-C™ microspheres were coated with a mAb specific for the μ-chain of human IgM (KPL) using a Luminex bead coupling kit (no deviation from manufacturer's instructions). The coupling reaction used a 4 μg/mL solution of the anti-μ mAb. The coated microspheres were added to Costar white polystyrene, 96-well plates (Corning) at about 2,000 microspheres/well. Next, serial dilutions of a confirmed-positive IgM serum sample from LASV- or EBOV-infected NHP were added to the coated microspheres. The plates were incubated at room temperature (RT) for 1 hour while shaking, and then washed three times with PBS containing 1% BSA and 0.1% Tween20 (PBS-BT). For FIG. 1 to FIG. 4, LASV or EBOV antigens from tissue culture supernatant were diluted with PBS-BT to working concentrations of $5.7 \times 10^5$ or $3.4 \times 10^6$, respectively, and added to the plates. For FIG. 5 to FIG. 8, a cocktail of recombinant LASV antigens (GPC and NP) or a cocktail of recombinant EBOV antigens (GP and VP40) was added to the plates. Each cocktail constituent was used at 10 ng/μL in PBS-BT. All plates were incubated at room temperature for 1 hour while shaking, and then washed three times with PBS-BT. Plates testing for the presence of LASV-specific IgM next received a cocktail of two biotinylated detector mAbs diluted to 4 μg/mL with PBS-BT. One mAb was specific for glycoprotein complex GPC (L52-2074-7A) and the other for nucleocapsid protein NP (L52-189-13). Plates testing for the presence of EBOV-specific IgM also received a cocktail of two biotinylated detector mAbs diluted to 4 μg/mL with PBS-BT. One mAb was specific for glycoprotein GP1 (DA01-A5-B11) and the other for VP40 (BMD04-BD07-AE11). After the respective cocktails were added, all plates were incubated at room temperature for 1 hour while shaking, and then washed three times with PBS-BT. Lastly, all plates received Steptavidin, R-phycoerythrin conjugate (Life Technologies) diluted to 4 μg/mL with PBS-BT, were incubated at room temperature for 1 hour while shaking, and then washed three times with PBS-BT. The fluorescent signal generated by each well was measured with the Luminex MAGPIX® system. For a result to be valid, a minimum of 50 beads/well had to be detected by the system.

ELISA Antigen Detection (Sandwich) Assays

Costar Serocluster™ vinyl, 96-well ELISA plates (Corning) were coated overnight at 4° C. with a mAb specific for the antigen of interest: L52-85-6-BG12 for LASV-GPC, L52-2159-15 for LASV NP, Z-DA06-AH05 for EBOV-GP, and M-GD06-A10A for EBOV-VP40. All coating antibodies were used at 4 μg/mL in PBS. After coating, serial dilutions of either LASV (for FIG. 11 to FIG. 14) or EBOV (for FIG. 15 to FIG. 18) tissue culture supernatant were made in PBS-S and added to the plates. The plates were incubated at 37° C. for 1 hour, and then washed three times with PBS-T. A biotinylated mAb (4 μg/mL in PBS-S) specific for the antigen of interest was then added: L-52-2074A for LASV-GPC, L52-189-13 for LASV-NP, DA01-A5-B11 for EBOV-GP, and BMD04-BD07-AE11 for EBOV-VP40. The plates were incubated at 37° C. for 1 hour, and then washed three times with PBS-T. Next, all plates received HRP-linked streptavidin (Thermo Fisher Scientific) diluted to 25 µg/mL with PBS-T, were incubated at 37° C. for 1 hour, and then washed three times with PBS-T. To derive the colorimetric reaction, ABTS® peroxidase substrate solution (KPL) was added and the plates were incubated at 37° C. for 1 hour. The optical densities (OD) were determined at 410 nm in an automated ELISA reader.

MAGPIX® Antigen Detection (Sandwich) Assays in Buffer

MagPlex-C™ microspheres were coated with a mAb specific for the antigen of interest: L52-85-6-BG12 for LASV-GPC, L52-2159-15 for LASV NP, Z-DA06-AH05 for EBOV-GP, and M-GD06-A10A for EBOV-VP40. All coating antibodies were used at 4 µg/mL in PBS. The coupling reactions were performed using a Luminex bead coupling kit (no deviation from manufacturer's instructions). The coated microspheres were added to Costar white polystyrene, 96-well plates (Corning) at about 2,000 microspheres/well. After coating, serial dilutions of either LASV (for FIG. 11 to FIG. 14) or EBOV (for FIG. 15 to FIG. 18) tissue culture supernatant were made in PBS-BT and added to the plates.

All plates were incubated at room temperature for 1 hour while shaking, and then washed three times with PBS-BT. A biotinylated mAb (4 µg/mL in PBS-BT) specific for the antigen of interest was then added: L-52-2074A for LASV-GPC, L52-189-13 for LASV-NP, DA01-A5-B11 for EBOV-GP, and BMD04-BD07-AE11 for EBOV-VP40. All plates were incubated at room temperature for 1 hour while shaking, and then washed three times with PBS-BT. Lastly, all plates received Steptavidin, R-phycoerythrin conjugate (Life Technologies) diluted to 4 µg/mL with PBS-BT, were incubated at room temperature for 1 hour while shaking, and then washed three times with PBS-BT. The fluorescent signal generated by each well was measured with the Luminex MAGPIX® system. For a result to be valid, a minimum of 50 beads/well had to be detected by the system.

Normalization and MAGPIX® Antigen Detection Assays in Spiked Human Serum

Antigen-detection of LASV-NP required two sets of MagPlex-C™ microspheres (with different internal labels). One set was coated with anti-LASV-NP mAb L52-2159-15. The other set was coated with a mAb specific for the M13 of bacteriophage (GE Lifesciences, #27942001). All coating antibodies were used at 4 µg/mL in PBS. The coupling reactions were performed using a Luminex bead coupling kit (no deviation from manufacturer's instructions). About 2000 microspheres from each set were added to every well of a Costar white polystyrene, 96-well plate. 96 unique, normal human serum samples (Covance, Princeton, N.J.) were diluted 1:5 in PBS-BT. Eight of these serum samples were randomly selected and received a serial dilution of LASV antigen (tissue culture supernatant). These 96 samples (88 normal, 8 spiked) were added individually to the 96 wells containing microspheres. The plate was incubated at room temperature for 1 hour while shaking, and then washed three times with PBS-BT. After washing, each well received a cocktail of two biotinylated detector mAbs diluted to 4 µg/mL with PBS-BT. One mAb was specific for nucleocapsid protein NP (L52-189-13) and the other is the same M13 mAb (GE Lifesciences, #27942001) used in microsphere coating. The plate was incubated at room temperature for 1 hour while shaking, and then washed three times with PBS-BT. Lastly, all plates received Steptavidin, R-phycoerythrin conjugate (Life Technologies) diluted to 4 µg/mL with PBS-BT, were incubated at room temperature for 1 hour while shaking, and then washed three times with PBS-BT. The signal generated by each well was measured with the Luminex MAGPIX® instrument. For a result to be valid, a minimum of 50 beads/well had to be detected by the system. The LASV-NP/M13-MFI ratio for each sample was obtained. The values are expressed as Z-scores, using the mean and standard deviation of all ratios from the experimental population.

EBOV-VP40 antigen-detection from spiked human serum was performed using the same general procedure as the LASV-NP protocol described above. Coating antibody: anti-EBOV-VP40 mAb M-HD06-A10A. Biotinylated detector antibody: anti-EBOV-VP40 mAb BMD04-BD07-AE11. Eight randomly selected serum samples received a serial dilution of EBOV antigen (tissue culture supernatant). The EBOV-VP40/M13-MFI ratio for each sample was obtained. The values are expressed as Z-scores, using the mean and standard deviation of all ratios from the experimental population.

Lower Limit of Detection (LLOD) Determination

Due to the rarity of some samples, a thorough statistical determination of LLOD could not be performed. Thus, for FIG. 1 to FIG. 18, the minimum threshold for a test measurement to be considered positive (LLOD) was set at 2.5 times the average negative control measurement.

Results

IgM-Detection Comparison with Native LASV and EBOV Antigens

The lower limit of detection (LLOD) of ELISA and MAGPIX® for both LASV- and EBOV-IgM detection assays were compared. The LLOD is defined as 2.5 times the average negative control measurement. Normally, IgM assays utilize native or recombinant viral antigens to detect antigen-specific IgM. The data in FIG. 1 to FIG. 4 represent assays, which used native viral antigens from tissue culture supernatant for the detection of virus-specific IgM.

Using the same LASV-specific reagents and parameters, the MAGPIX® platform showed a more sensitive LLOD when testing a known LASV IgM-positive NHP serum sample FIG. 1 and FIG. 2). ELISA displayed a LLOD when the IgM-positive serum was diluted to 1:2,500. For the same serum sample, the MAGPIX® platform displayed a LLOD at a 1:25,000 dilution.

Figures 3, 4:
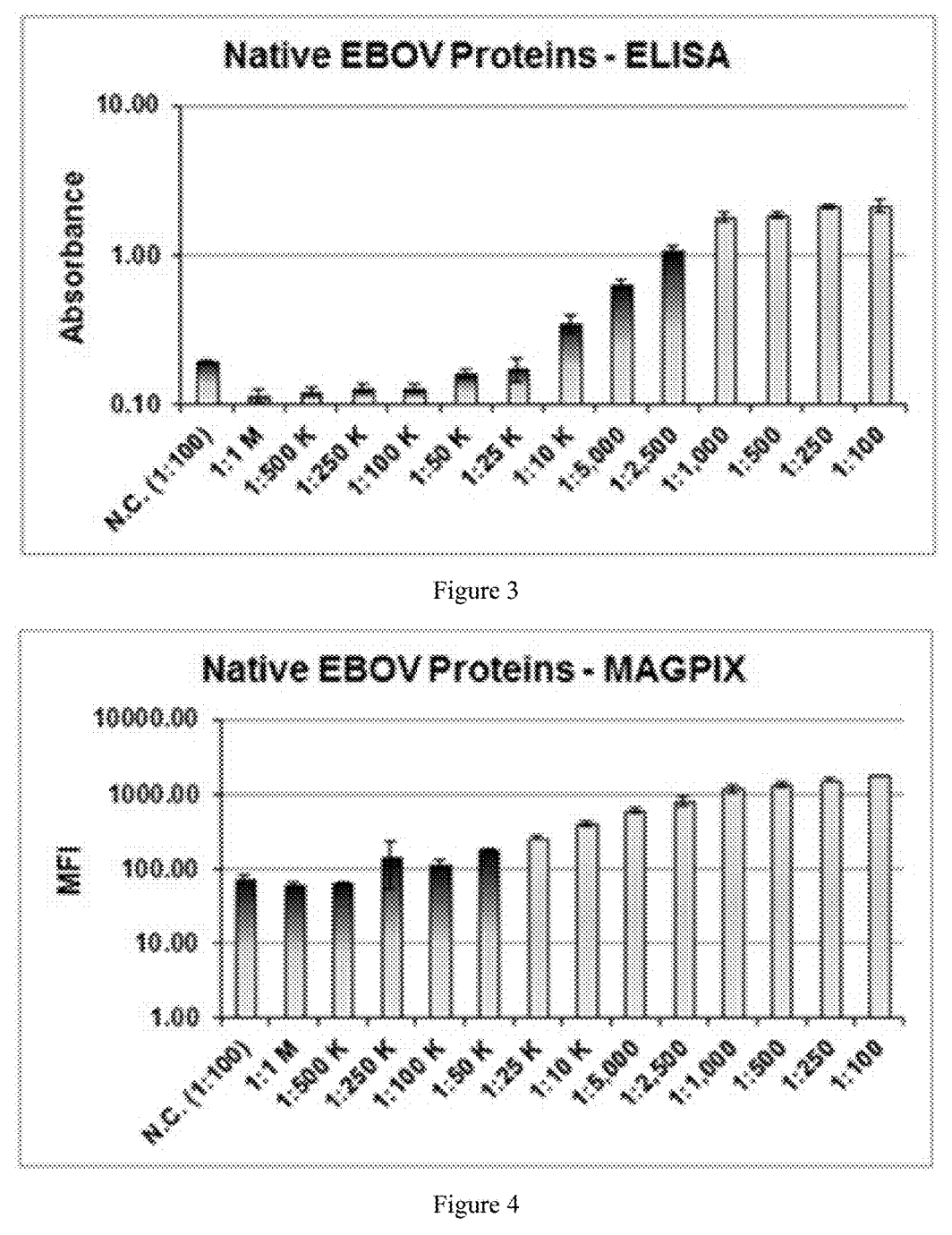

For the EBOV-IgM detection assay (using a known IgM-positive NHP serum sample), an ELISA LLOD was observed when the serum was diluted at 1:5,000 (FIG. 3 and FIG. 4). The same assay performed on the MAGPIX® platform showed a LLOD of 1:25,000.

IgM-Detection Comparison with Recombinant LASV and EBOV Antigens

Figures 5, 6:
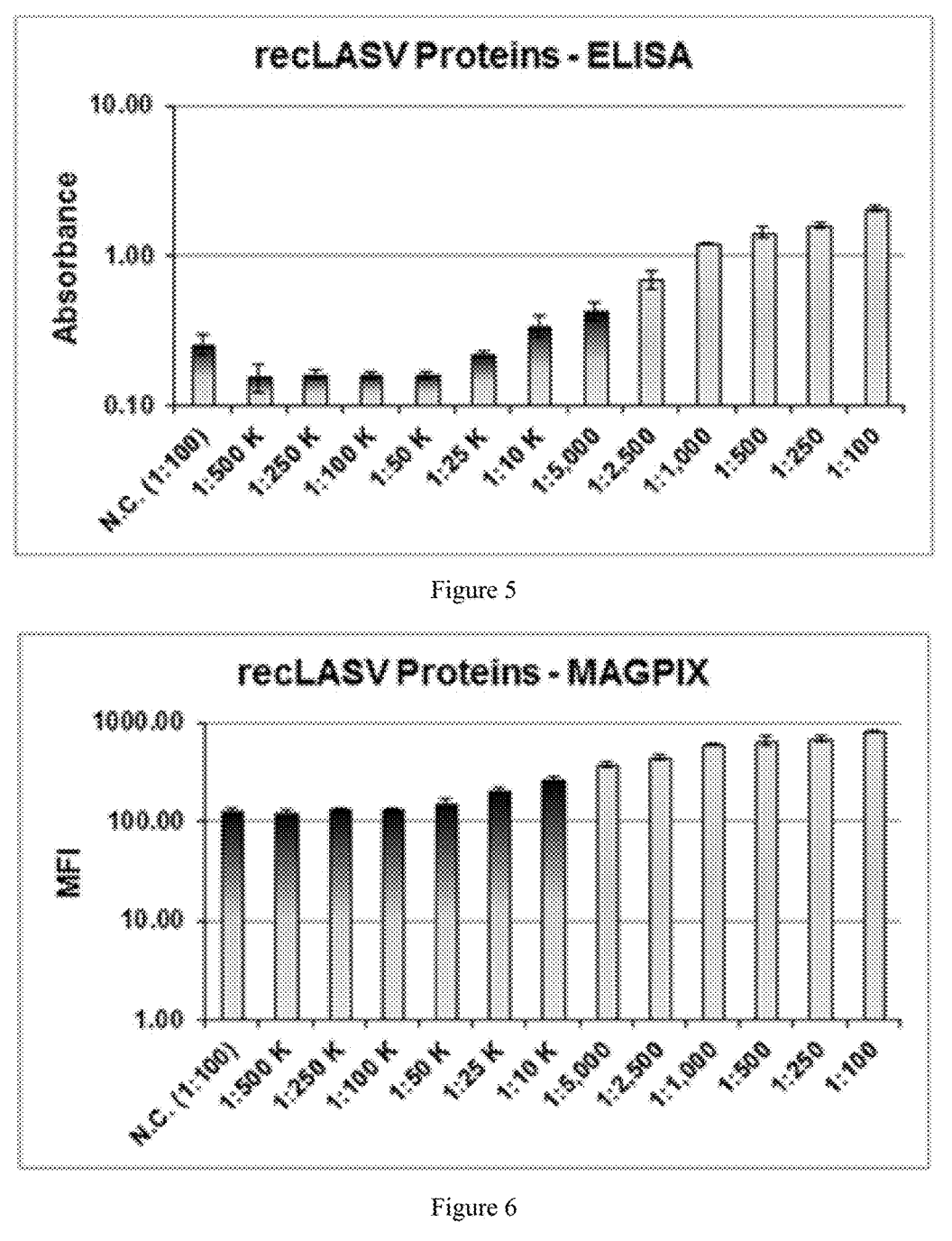
Figures 7, 8:
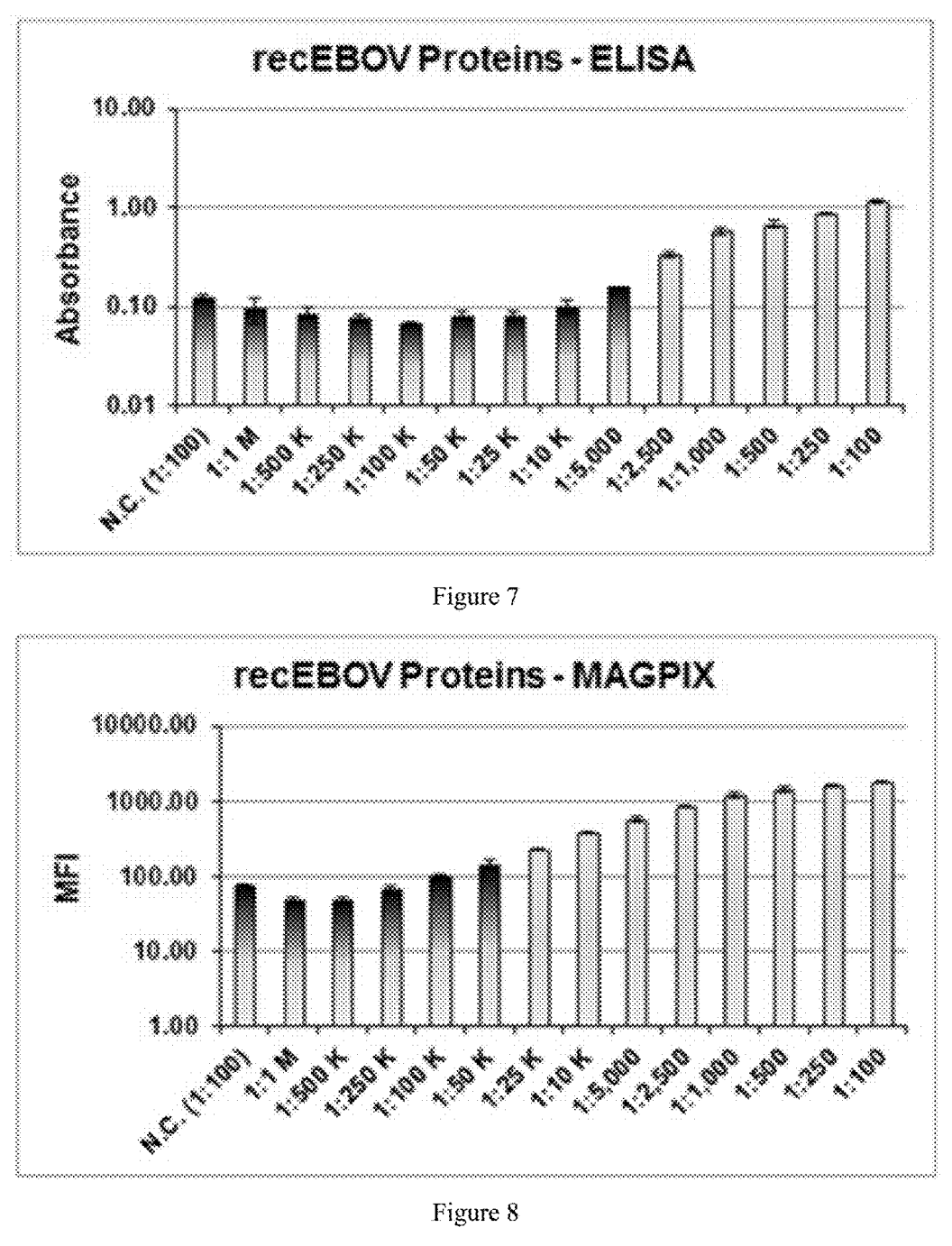

Since recombinant antigens are used routinely in IgM-detection assays as well as native antigens, the assays shown in FIG. 1 to FIG. 4 were repeated substituting tissue culture supernatant with a purified recombinant protein mixture from LASV (recGPC and recNP) or EBOV (recGP and recVP40). The ELISA assay LLOD was observed when the LASV-IgM positive serum sample was diluted to 1:2,500 (FIG. 5 and FIG. 6). Comparatively, the MAGPIX® assay LLOD was observed when the LASV-IgM serum sample was diluted to 1:5,000. An IgM-detection assay for EBOV using recombinant antigens displayed a similar trend (FIG. 7 and FIG. 8). The ELISA LLOD was observed at a 1:2,500 dilution of IgM positive serum, while the MAGPIX® assay LLOD was observed at a 1:25,000 dilution of IgM positive serum.

IgM-Detection Consistency with MAGPIX®

Figures 9, 10:
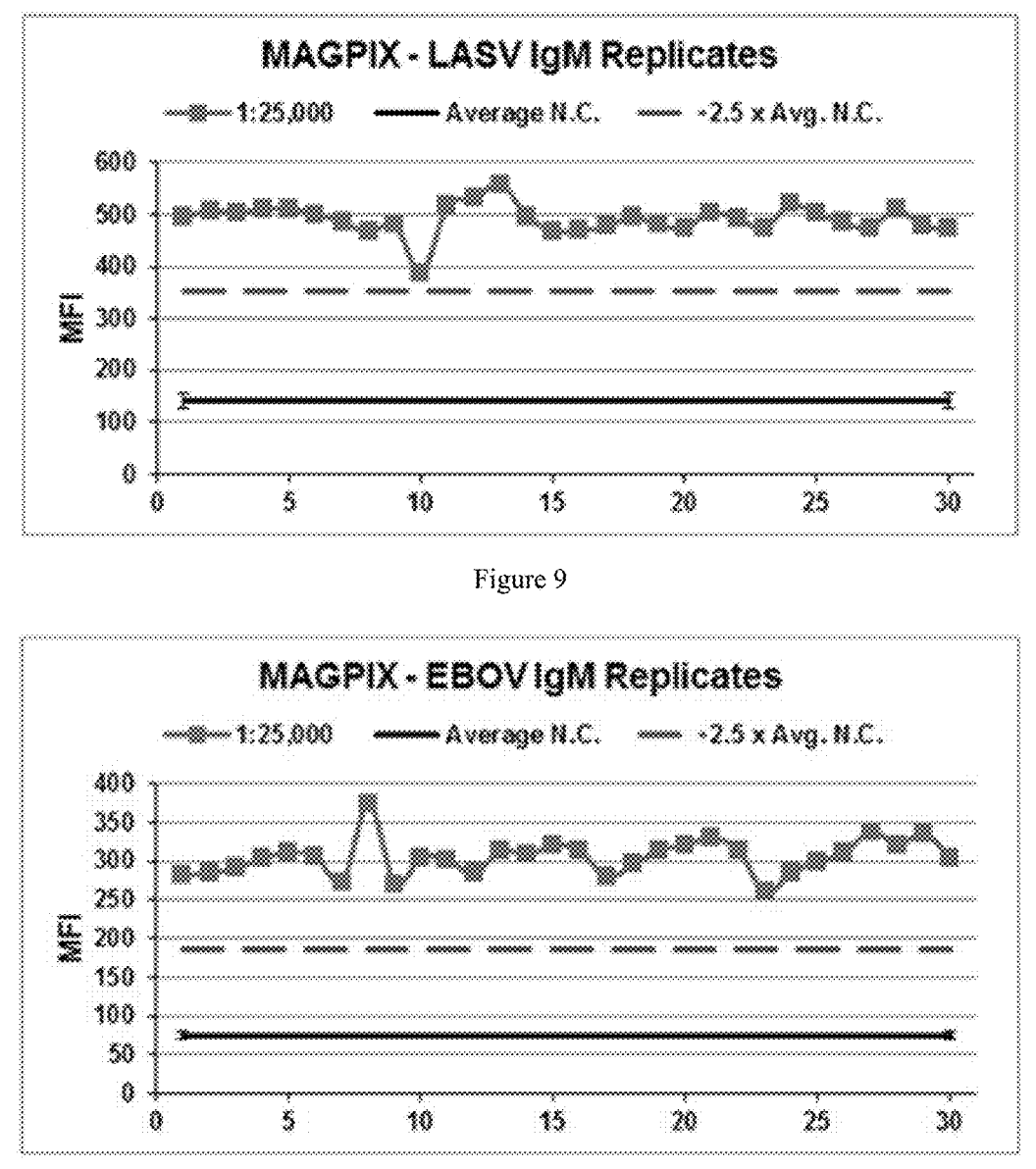

To test the MAGPIX® consistency at the LLOD for both LASV- and EBOV-IgM detection, native antigens were used and each IgM-positive serum sample was diluted to the LLOD (1:25,000 for LASV and 1:25,000 for EBOV, FIG. 1 to FIG. 4). This was repeated 30 times and these replicates were tested on the MAGPIX® platform. Also, 30 unique negative human serum samples were tested to observe possible background fluctuations caused by intrinsic matrix properties that can exist between different serums (FIG. 9 and FIG. 10).

To obtain a measurement of reproducibility for the 1:25:000 samples and the N.C. samples, the percent coefficient of variance (% CV) was determined for both groups. Regarding LASV 1:25,000 replicates, the % CV was 6% while the negative control samples had a % CV of 10%. Regarding the EBOV replicates, the % CV for the 1:25,000 spiked samples was 8% while negative control samples had a % CV of 5%.

LASV Antigen-Detection Comparison in Buffer

The ELISA and MAGPIX® platforms were compared using antigen-detection assays with native antigen as target and mAbs reactive to LASV-GPC, LASV-NP, EBOV-GP, and EBOV-VP40. FIG. 11 to FIG. 14 show LLOD determinations for LASV-GPC and LASV-NP.

Figure 12:
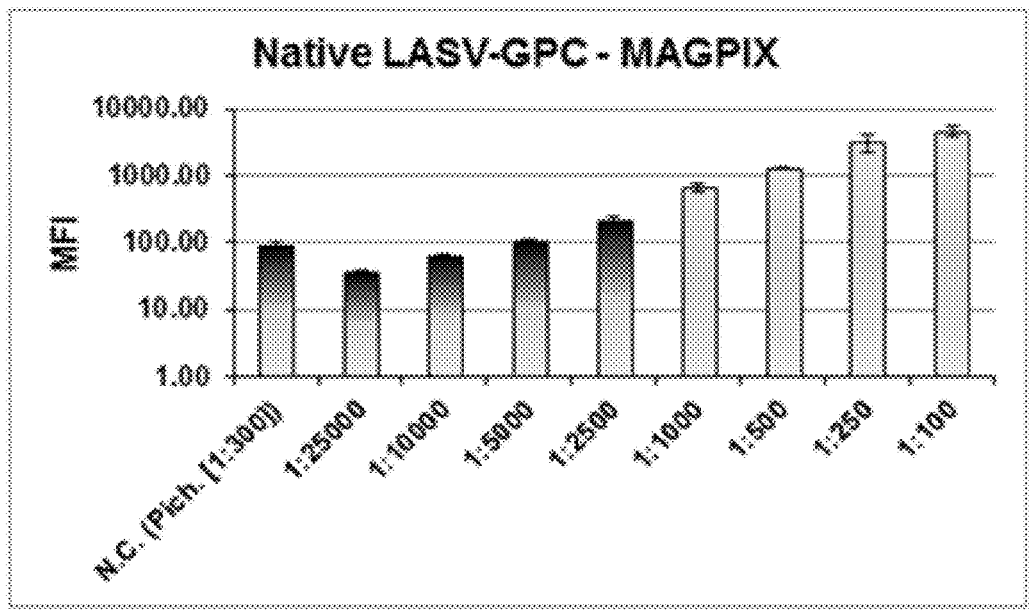
Figures 13, 14:
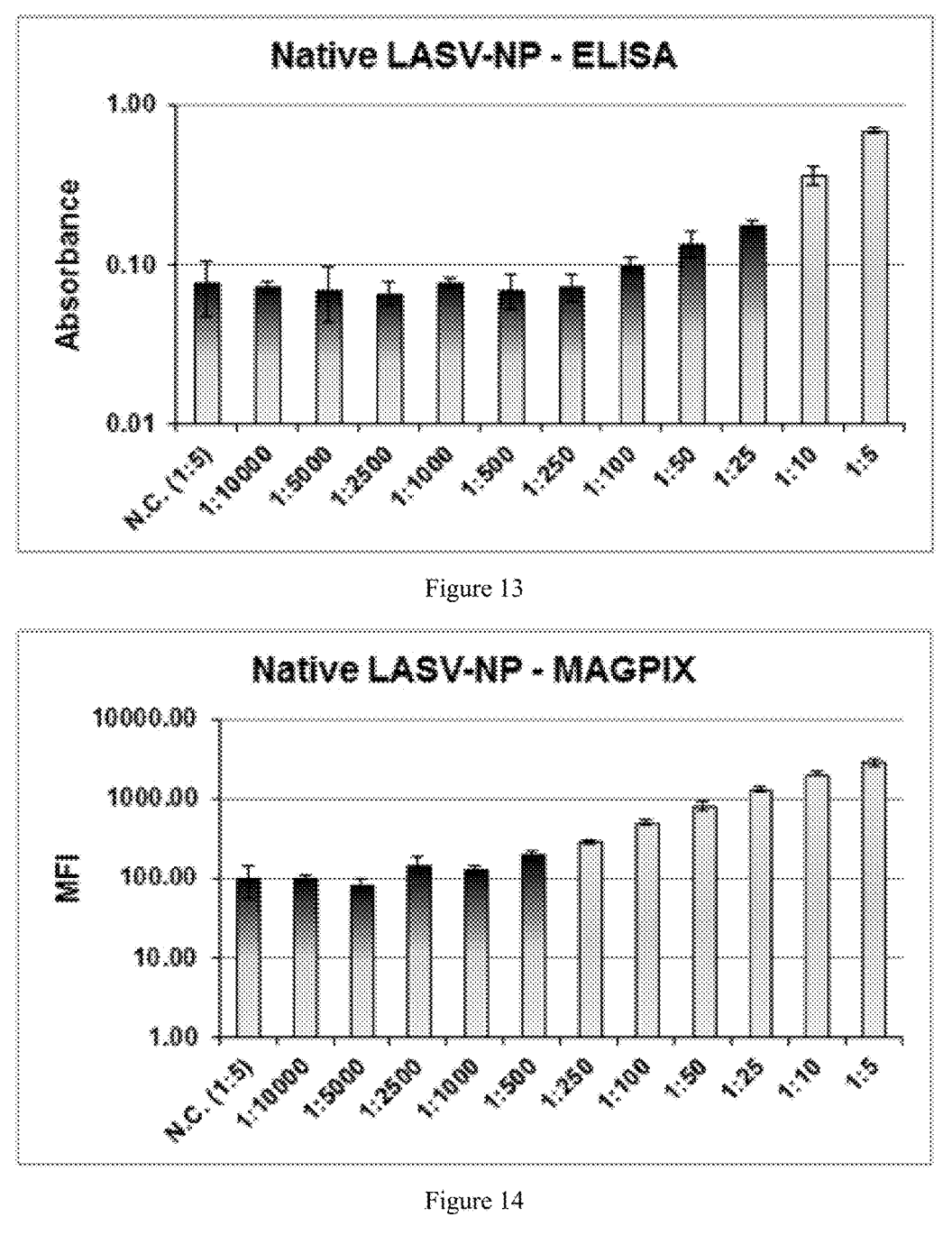

The LASV-GPC data show that the ELISA LLOD is reached at a dilution of 1:250, which corresponds to $5 \times 10^6$ pfu/mL (FIG. 11 and FIG. 12). The MAGPIX® platform detected GPC at a maximum dilution of 1:1,000, corresponding to a LLOD of $1.25 \times 10^6$ pfu/mL. The LASV-NP data show that ELISA detected NP at a maximum dilution of 1:10, corresponding to a LLOD of $2.3 \times 10^5$ pfu/mL (FIG. 13 and FIG. 14). In turn, the MAGPIX® platform detected LASV-NP at a dilution of 1:250, corresponding to a LLOD of $9.2 \times 10^3$ pfu/mL.

EBOV Antigen-Detection Comparison in Buffer

Figures 15, 16:
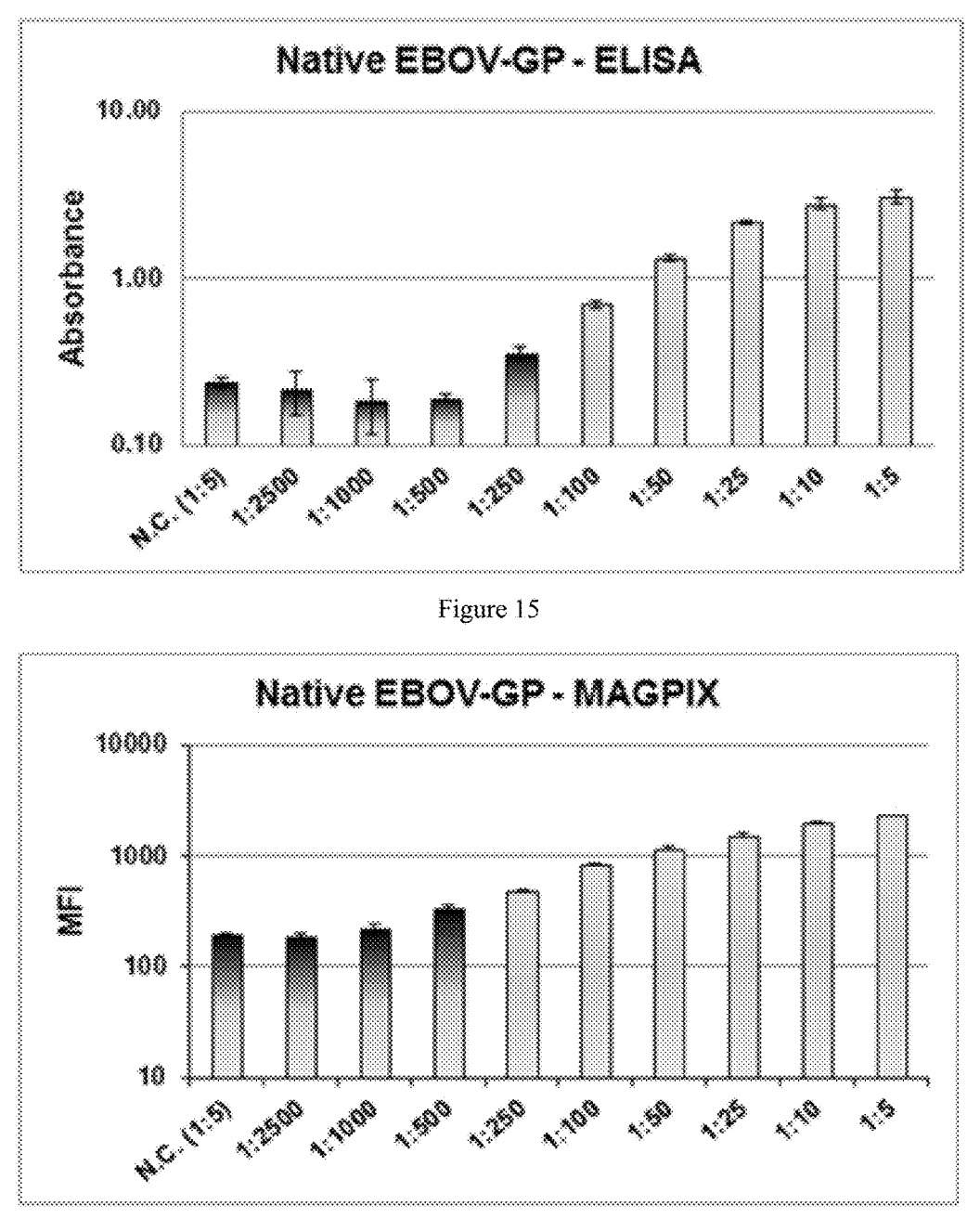
Figures 17, 18:
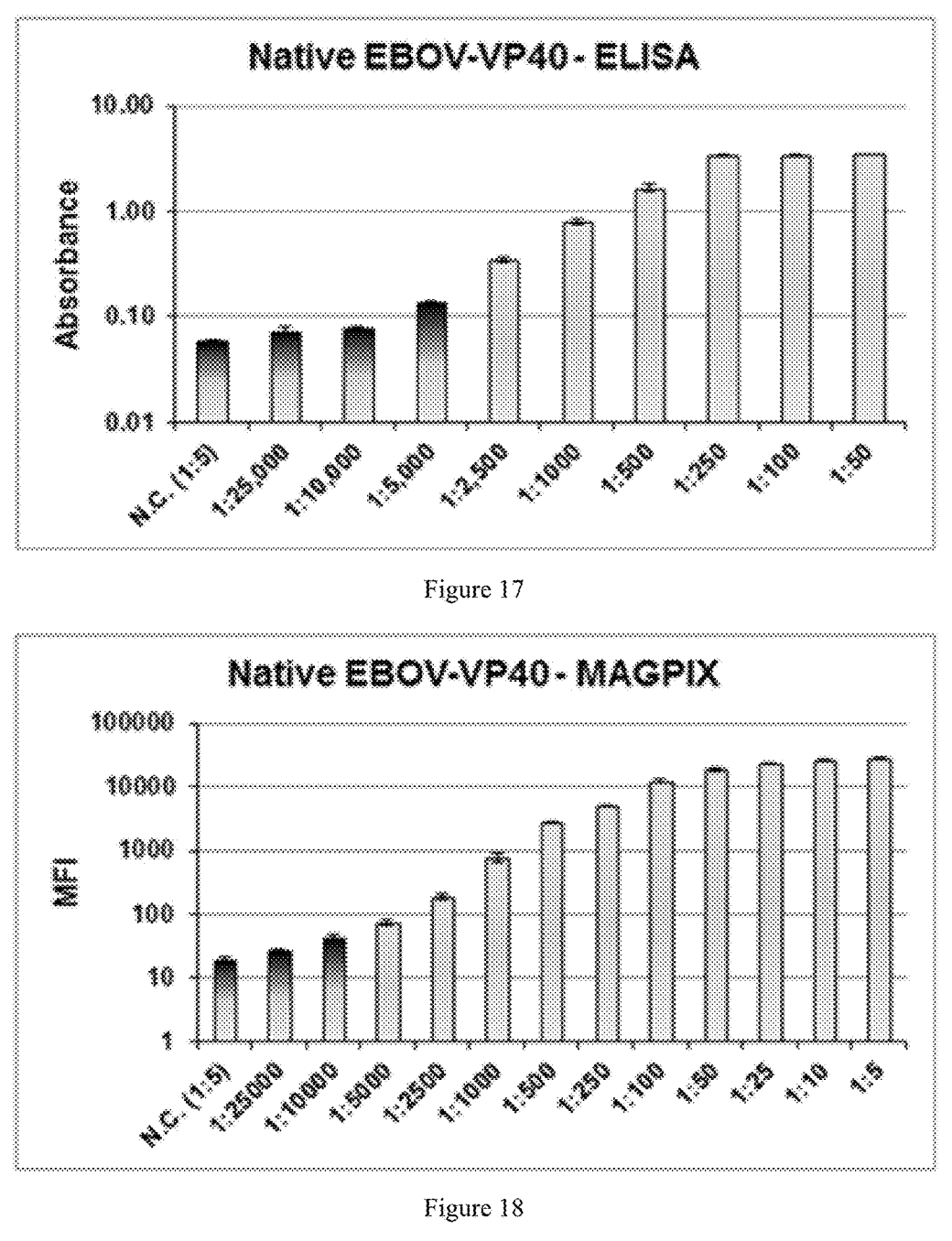

The LLOD of EBOV antigen-detection assays among both platforms was also determined. The EBOV-GP data demonstrate that the ELISA LLOD was located at a dilution of 1:100, corresponding to a LLOD of $1.7 \times 10^5$ pfu/mL (FIG. 15 and FIG. 16). The MAGPIX® LLOD was achieved at a dilution of 1:250, corresponding to $6.8 \times 10^4$ pfu/mL. The EBOV-VP40 data demonstrate that the ELISA LLOD was reached at a dilution of 1:2,500, corresponding to $6.8 \times 10^3$ pfu/mL (FIG. 17 and FIG. 18). The MAGPIX® LLOD was located at the dilution of 1:5,000, corresponding to $3.4 \times 10^3$ pfu/mL.

Reproducibility of Normalization and MAGPIX® LASV-NP Antigen-Detection

The assays depicted in FIG. 11 to FIG. 18 were performed in a simple matrix (i.e., buffer). Clinical samples will generally contain serum, which can present background matrix effects. Not only can these matrix effects greatly reduce the sensitivity of an immunoassay, they can also produce significantly different results from one normal clinical sample to another because of the intrinsic characteristics of the samples themselves. In turn, different clinical samples spiked with equivalent amounts of positive control antigen can yield significantly different LLODs. This lack of consistency from sample to sample is a common pitfall of ELISA. Reproducibility of an ELISA assay that is typically considered "adequate" generates a coefficient of variance of 20%, and sometimes up to 30%. These "matrix effects" have also been observed with the MAGPIX® platform when attempting to reproduce the data in FIG. 11 to FIG. 18 using serum instead of buffer (data not shown). Therefore, because of this issue, it is extremely difficult to determine the consistency of an antigen-detection assay between multiple serum samples.

To circumvent this issue, the multiplexing capability of the MAGPIX® platform was leveraged. For each sample, two separate assays were performed in the same well of a 96-well plate. One was an antigen-detection assay for LASV-NP. The other was an antigen-detection assay for bacteriophage M13 protein, which served as an internal control since it is unlikely any human sample will contain the phage protein M13. The assumption behind the feasibility of this method was: matrix effects of a sample should cause a direct relationship to form between the MFI of the LASV-NP detection assay and the MFI of the M13 detection assay. In other words, when the background of a sample is relatively high, the MFI for the LASV-NP assay and the M13 assay will be relatively high; when the background of a sample is relatively low, the MFI for the LASV-NP assay and the M13 assay will be relatively low. With this direct correlation, a ratio between the LASV-NP MFI and M13 MFI could be used to normalize the background matrix effects. For example, serum samples spiked with positive antigen (LASV-NP) should create a LASV-NP/M13 MFI ratio that falls outside of a normal distribution of ratios created by a population of unique, unspiked samples.

Figure 19:
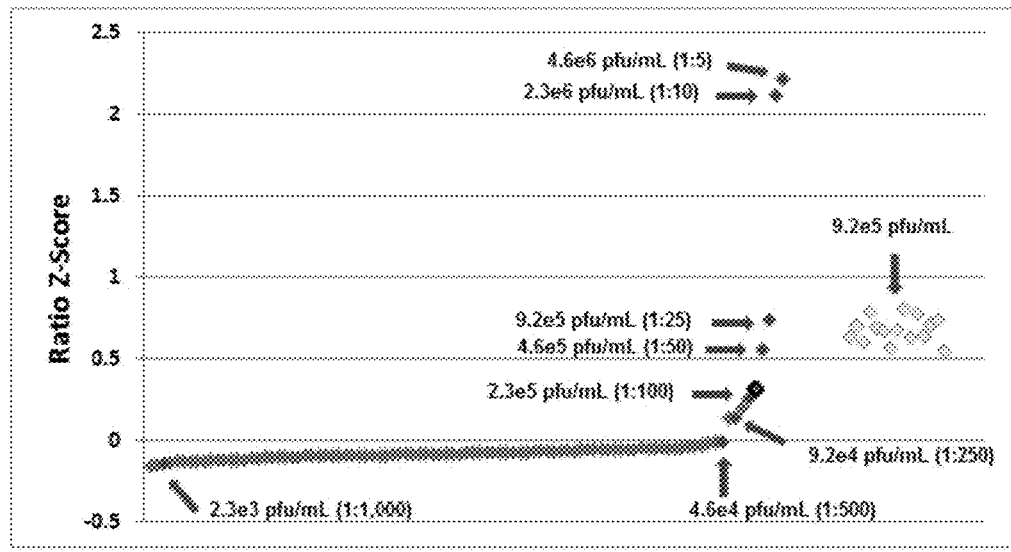

To evaluate this method, a population of 96 unique, normal human serum samples was tested. Of these 96, eight were randomly spiked with varying concentrations of LASV tissue culture supernatant (similar to those in FIG. 13 and FIG. 14 (1:5-1:1,000)). The Z scores for the LASV-NP/M13 MFI ratios were calculated and arranged smallest to largest (FIG. 19). Here, the 1:25 dilution ($9.2 \times 10^5$ pfu/mL) was selected as the LLOD because it was the minimal amount of antigen required to produce a ratio Z-score that was 1 Z-score above the highest unspiked ratio Z-score (FIG. 19, blue data point outlined in black).

Using this LLOD, the consistency of the MAGPIX® platform for LASV-NP antigen-detection in a complex clinical matrix was determined. To do this, 15 unique, normal human serum samples were spiked with LASV tissue culture supernatant at $9.2 \times 10^5$ pfu/mL (1:25 dilution). The LASV-NP/M13 ratios for the 15 samples were determined and analyzed with the previous 96 samples (FIG. 19, yellow data points). The consistency of the results was measured using % CV. The % CV for these 15 samples was 12%.

Reproducibility of Normalization and MAGPIX® EBOV-VP40 Antigen-Detection

Figure 20:
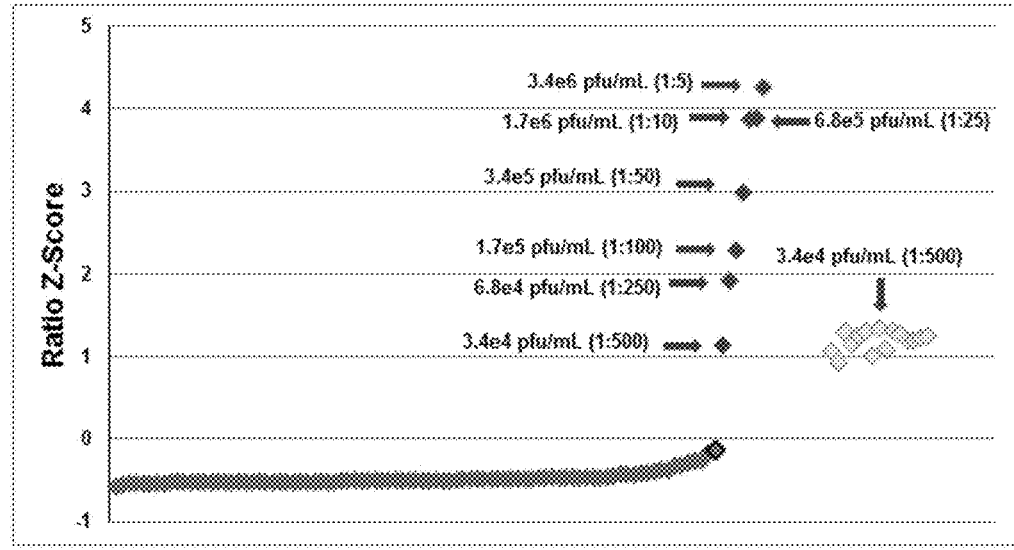

The same experimental setup used for LASV-NP antigen detection reproducibility was tested for EBOV-VP40 antigen-detection. The EBOV-VP40/M13-MFI ratio for 96 unique, normal human serum samples was determined (eight of the samples were randomly spiked with EBOV tissue culture supernatant as in FIG. 17 and FIG. 18 (1:5-1:500)). The concentrations of EBOV of the 8 samples were: $3.4 \times 10^6$ pfu/mL, $1.7 \times 10^6$ pfu/mL, $6.8 \times 10^5$ pfu/mL, $3.4 \times 10^5$ pfu/mL, $1.7 \times 10^5$ pfu/mL, $6.8 \times 10^4$ pfu/mL, and $3.4 \times 10^4$ pfu/mL. The Z scores for the EBOV-VP40/M13 MFI ratios were calculated and arranged smallest to largest (FIG. 20). Here, the 1:500 ($3.4 \times 10^5$ pfu/mL) dilution was selected as the LLOD because it was the minimal amount of antigen required to produce a ratio Z-score that was 1 Z-score above the highest unspiked ratio Z-score (FIG. 20, blue data point outlined in black).

Using this LLOD, the consistency of the MAGPIX® platform for EBOV-VP40 antigen-detection in a complex clinical matrix was determined. To do this, 15 unique, normal human serum samples were spiked with LASV tissue culture supernatant at $3.4 \times 10^5$ pfu/mL (1:500 dilution). The consistency of the results was measured using % CV. The EBOV-VP40/M13 ratios for the 15 samples were determined and analyzed with the previous 96 samples (FIG. 20, yellow data points). The % CV for these 15 samples was 10%.

Further Analysis of Normalization Method

After spiking, all 96 samples (including the 8 spiked samples) were assayed using the MAGPIX® platform with and without the normalization method using mAb against M13 as described above.

Figure 21:
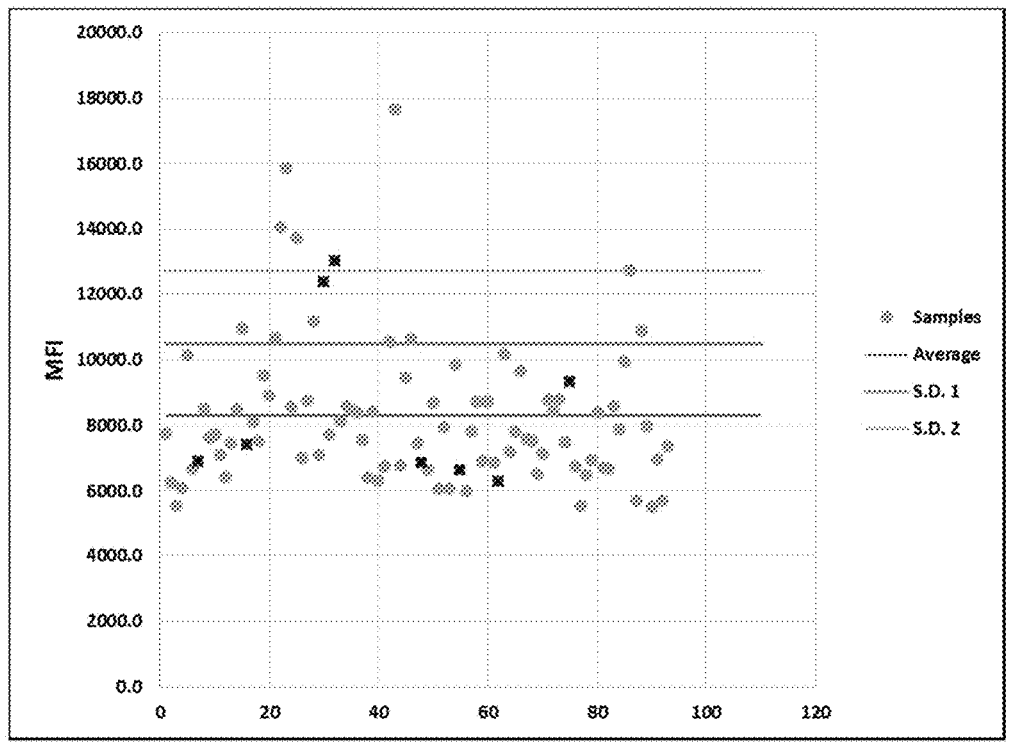

The mean fluorescent intensities (MFI) for EBOV and M13 were determined for each sample in triplicate. FIG. 21 shows the MFI of the samples without normalization. As shown in FIG. 21, the circles are unspiked samples, the squares with the X are the spiked samples, and the horizontal lines from bottom to top are: the mean MFI of all samples, one standard deviation above the mean MFI, two standard deviations above the mean MFI, respectively.

Figure 22:
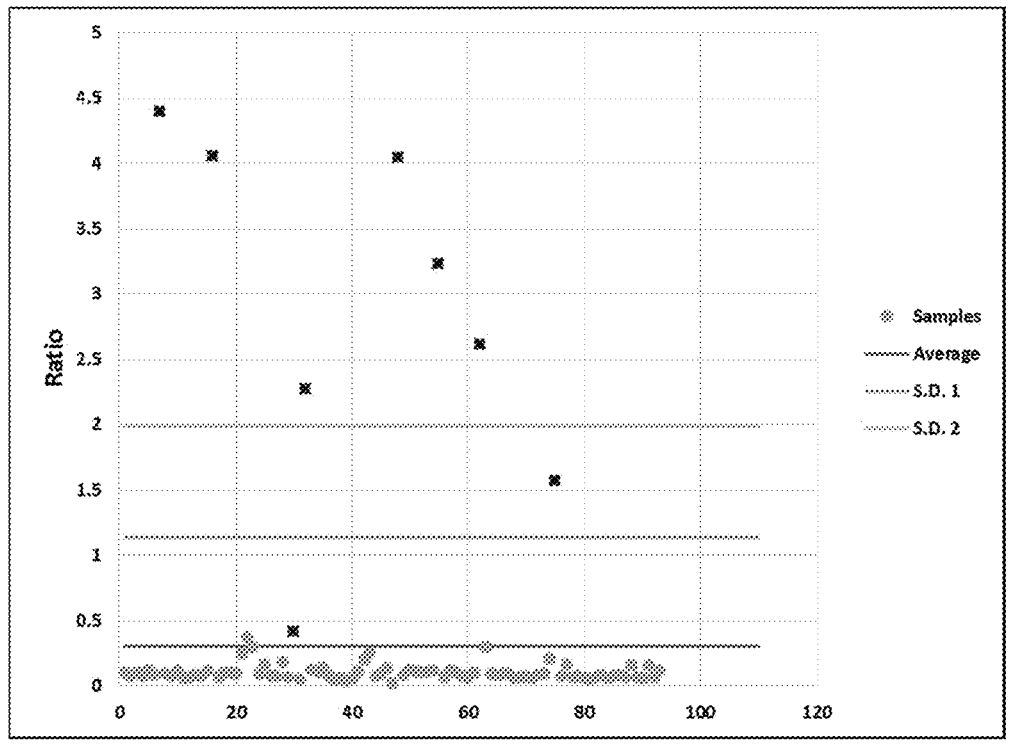

The ratio of the MFI of EBOV/M13 (normalized MFI) for each sample was calculated and plotted. See FIG. 22. As shown in FIG. 22, the circles are unspiked samples, the squares with the X are the spiked samples, and the horizontal lines from bottom to top are: the mean MFI of all samples, one standard deviation above the mean MFI, two standard deviations above the mean MFI, respectively.

Figure 23:
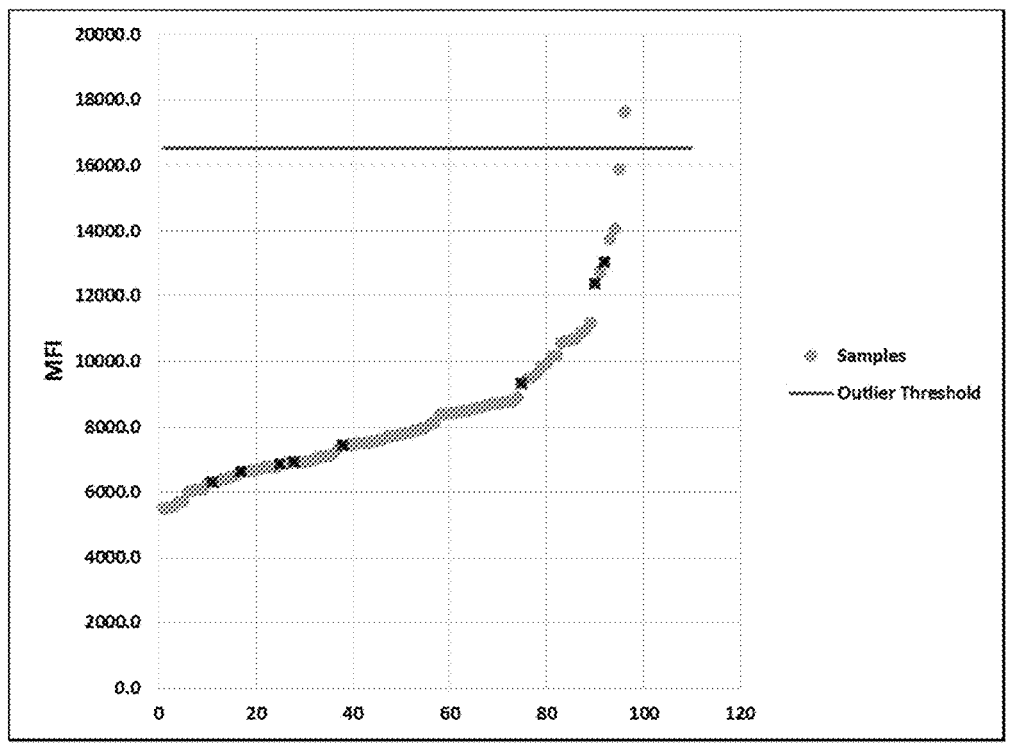

The outlier threshold of the samples without normalization and with normalization were determined using interquartile statistical methods. FIG. 23 shows the MFI values (without normalization) of the 96 samples. The horizontal line indicates the outlier threshold that is the interquartile range multiplied by 4 added to the MFI value demarcating the start of the 4th quartile (4×IQR+MFI value starting the 4th quartile).

Figure 24:
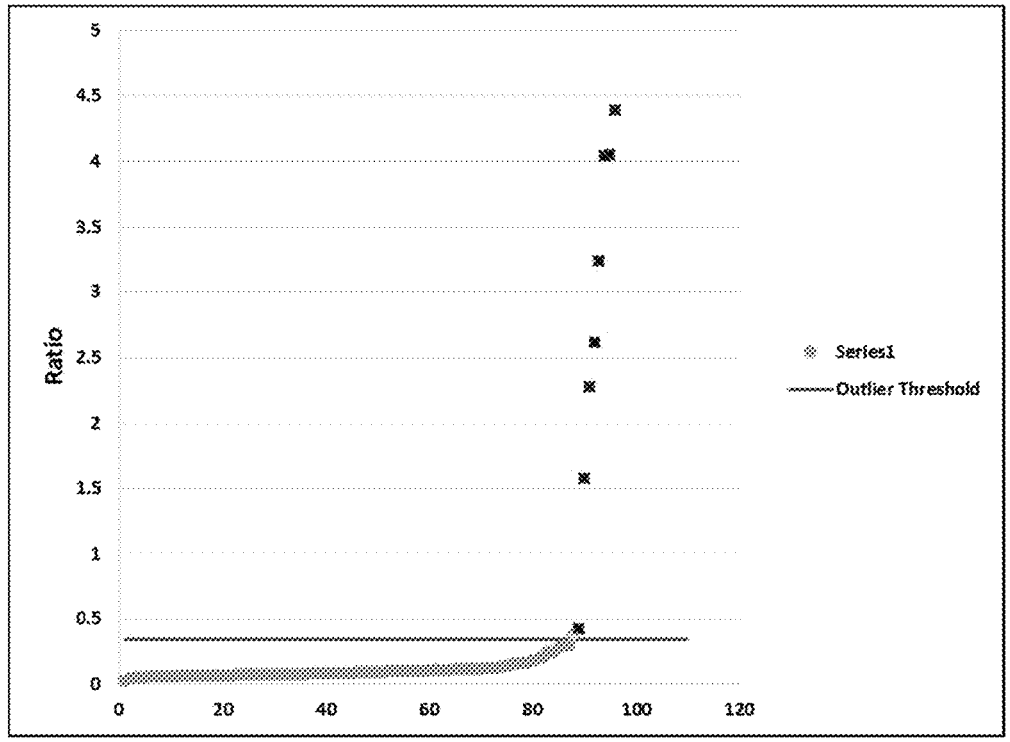

FIG. 24 shows the ratio of the MFI of EBOV/M13 (normalized MFI) for each sample. The horizontal line indicates the outlier threshold that is the interquartile range multiplied by 4 added to the ratio of the MFI EBOV/M13 value demarcating the start of the 4th quartile (4×IQR+MFI EBOV/M13 ratio starting the 4th quartile).

For the standard deviation plots (FIG. 21 and FIG. 22), samples above the mean should be positive for EBOV and samples at the mean and below should be negative. For the interquartile range plots (FIG. 23 and FIG. 24), samples above the outlier threshold should be positive for EBOV and samples below should be negative.

As shown in FIG. 21 and FIG. 23, without normalization according to the present invention, multiplex assays (especially those performed on serum samples) provides false negative and false positive results. Using the normalization method of the present invention, however, resulted in only one false positive and no false negatives by both the standard deviation and interquartile range methods. Thus, as shown in FIG. 22 and FIG. 24, results in 100% accuracy in detecting the presence of a target (in this case EBOV) with less than 1% false positives.

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for obtaining a normalized measured amount of a given target in a sample using a multiplex immunoassay which comprises
    measuring the amount of the given target in the sample by contacting the sample with a detection reagent for the given target,
    measuring the amount of an M13 bacteriophage protein in the sample using an antibody specific for the M13 bacteriophage protein, and
    obtaining the normalized measured amount of the given target by calculating the ratio of the measured amount of the given target to the measured amount of the M13 bacteriophage protein.

2. A method for identifying a sample as containing or not containing a given target which comprises
    using a multiplex immunoassay to measure the amount of the given target in the sample by contacting the sample with a detection reagent for the given target and measure the amount of an M13 bacteriophage protein in the sample by contacting the sample with an antibody specific for the M13 bacteriophage protein,
    obtaining the normalized measured amount of the given target by calculating the ratio of the measured amount of the given target to the measured amount of the M13 bacteriophage protein, and
    identifying the sample as containing the given target where the normalized measured amount of the given target is a positive number.

3. The method of claim 1, wherein the given target is an antigen from an *Ebolavirus* spp. or an *Arenavirus* spp.

4. The method of claim 1, wherein the given target is (a) *Ebola virus* or a protein thereof, or (b) *Lassa virus* or a protein thereof.

5. The method of claim 1, wherein the antibody is a monoclonal antibody.

6. The method of claim 1, wherein the antibody was raised against the M13 bacteriophage protein or an M13 bacteriophage.

7. The method of claim 1, wherein a microsphere comprising a fluorophore and the antibody specific for the M13 bacteriophage protein is employed.

8. The method of claim 7, wherein the microsphere is a magnetic or a paramagnetic microsphere.

9. The method of claim 7, wherein the microsphere is provided in a kit and is packaged together with one or more reagents for performing the multiplex immunoassay.

10. The method of claim 2, wherein the given target is an antigen from an *Ebolavirus* spp. or an *Arenavirus* spp.

11. The method of claim 2, wherein the given target is (a) *Ebola virus* or a protein thereof, or (b) *Lassa virus* or a protein thereof.

12. The method of claim 2, wherein the antibody is a monoclonal antibody.

13. The method of claim 2, wherein the antibody was raised against the M13 bacteriophage protein or an M13 bacteriophage.

14. The method of claim 2, wherein a microsphere comprising a fluorophore and the antibody specific for the M13 bacteriophage protein is employed.

15. The method of claim 14, wherein the microsphere is a magnetic or a paramagnetic microsphere.

16. The method of claim 14, wherein the microsphere is provided in a kit and is packaged together with one or more reagents for performing the multiplex immunoassay.

\* \* \* \* \*